US00PP32401P2

(12) United States Plant Patent
Arts

(10) Patent No.: US PP32,401 P2
(45) Date of Patent: Oct. 27, 2020

(54) ***HYDRANGEA* PLANT NAMED 'H218917'**

(50) Latin Name: *Hydrangea macrophylla*
Varietal Denomination: H218917

(71) Applicant: HYDRANGEA BREEDERS ASSOCIATION B.V., De Kwakel (NL)

(72) Inventor: Niels Arts, Aalsmeer (NL)

(73) Assignee: Hydrangea Breeders Association B.V., De Kwakel (NL)

( * ) Notice: Subject to any disclaimer, the term of this patent is extended or adjusted under 35 U.S.C. 154(b) by 0 days.

(21) Appl. No.: 16/602,105

(22) Filed: Aug. 7, 2019

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 6/48
See application file for complete search history.

(56) References Cited

PUBLICATIONS

UPOV hit on *Hydrangea* plant named, 'H218917', QZ PBR 20183314, application dated Dec. 14, 2018.*

* cited by examiner

*Primary Examiner* — Anne Marie Grunberg
(74) *Attorney, Agent, or Firm* — C. A. Whealy

(57) ABSTRACT

A new and distinct cultivar of *Hydrangea* plant named 'H218917', characterized by its upright and uniformly mounded plant habit; vigorous growth habit and rapid growth rate; freely branching habit with strong, thick and sturdy stems; freely and uniformly flowering habit; lacecap-type inflorescences with numerous double sterile flowers that are red purple in color; and good postproduction longevity.

3 Drawing Sheets

Botanical designation: *Hydrangea macrophylla.*
Cultivar denomination: 'H218917'.

BACKGROUND OF THE INVENTION

The present invention relates to a new and distinct cultivar of *Hydrangea* plant, botanically known as *Hydrangea macrophylla*, commercially referred to as a lacecap-type *Hydrangea* and hereinafter referred to by the name 'H218917'.

The new *Hydrangea* plant is a product of a planned breeding program conducted by the Inventor in De Kwakel, The Netherlands and Lengerich, Germany. The objective of the breeding program was to create new strong and freely-branching *Hydrangea* plants with strong sturdy stems, uniform flowering habit, large inflorescences with numerous showy sterile flowers, attractive sterile flower color and good postproduction longevity.

The new *Hydrangea* plant originated from a cross-pollination made by the Inventor in March, 2014 in De Kwakel, The Netherlands, of a proprietary selection of *Hydrangea macrophylla* identified as code number 11-0240-016, not patented, as the female, or seed, parent with a proprietary selection of *Hydrangea macrophylla* identified as code number 11-0238-005, not patented, as the male, or pollen, parent. The new *Hydrangea* plant was discovered and selected by the Inventor as a single flowering plant from within the progeny of the stated cross-pollination in a controlled greenhouse environment in Lengerich, Germany in March, 2015.

Asexual reproduction of the new *Hydrangea* plant by vegetative tip cuttings in a controlled environment in De Kwakel, The Netherlands since April, 2016 has shown that the unique features of this new *Hydrangea* plant are stable and reproduced true to type in successive generations.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'H218917'. These characteristics in combination distinguish 'H218917' as a new and distinct *Hydrangea* plant:

1. Upright and uniformly mounded plant habit.
2. Vigorous growth habit and rapid growth rate.
3. Freely branching habit with strong, thick and sturdy stems.
4. Freely and uniformly flowering habit.
5. Lacecap-type inflorescences with numerous double sterile flowers that are red purple in color.
6. Good postproduction longevity.

Plants of the new *Hydrangea* can be compared to plants of the female parent selection. Plants of the new *Hydrangea* differ primarily from plants of the female parent selection in sterile flower type as plants of the new *Hydrangea* have double sterile flowers whereas plants of the female parent selection have single sterile flowers.

Plants of the new *Hydrangea* can be compared to plants of the male parent selection. Plants of the new *Hydrangea* differ primarily from plants of the male parent selection in sterile flower type as plants of the new *Hydrangea* have double sterile flowers whereas plants of the male parent selection have single sterile flowers.

Plants of the new *Hydrangea* can be compared to plants of the *Hydrangea macrophylla* 'H213904', disclosed in U.S. Plant Pat. No. 26,454. In side-by-side comparisons, plants of the new *Hydrangea* differ primarily from plants of 'H213904' in the following characteristics:

1. Plants of the new *Hydrangea* are shorter than plants of 'H213904'.
2. Plants of the new *Hydrangea* have smaller leaves than plants of 'H213904'.
3. Plants of the new *Hydrangea* have broader panicles than plants of 'H213904'.
4. Plants of the new *Hydrangea* have double sterile flowers whereas plants of 'H213904' have single sterile flowers.
5. Plants of the new *Hydrangea* have not been observed to develop fertile flowers whereas plants of 'H213904' develop fertile flowers.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet is a side perspective view of a typical flowering plant of 'H218917'.

The photograph on the second sheet is a close-up view of a typical inflorescence of 'H218917'.

The photograph on the third sheet is a top perspective view of a typical flowering plant of 'H218917' that has been "blued" (left) that is, treated with aluminum sulfate, and a top perspective view of a typical flowering plant of 'H218917' that has not been "blued" (right) that is, not treated with aluminum sulfate.

DETAILED BOTANICAL DESCRIPTION

Plants used in the aforementioned photographs and in the following description were grown during the late spring and early summer in 15-cm containers in a glass-covered greenhouse in De Kwakel, The Netherlands and under cultural practices typical of commercial *Hydrangea* production. During the production of the plants, day and night temperatures averaged 17° C. Plants of the new *Hydrangea* were one year old when the photographs and description were taken. Plants of the new *Hydrangea* can be successfully treated with aluminum sulfate to "blue" the inflorescences. In the following description, color references are made to The Royal Horticultural Society Colour Chart, 2015 Edition, except where general terms of ordinary dictionary significance are used.

Botanical description: *Hydrangea macrophylla* 'H218917'.

Parentage:

*Female, or seed, parent*.—Proprietary selection of *Hydrangea macrophylla* identified as code number 11-0240-016, not patented.

*Male, or pollen, parent*.—Proprietary selection of *Hydrangea macrophylla* identified as code number 11-0238-005, not patented.

Propagation:

*Type cutting*.—By vegetative tip cuttings.

*Time to initiate roots, summer*.—About two weeks at temperatures about 23° C.

*Time to initiate roots, winter*.—About 18 days at temperatures about 20° C.

*Time to produce a rooted young plant, summer*.—About four weeks at temperatures about 23° C.

*Time to produce a rooted young plant, winter*.—About five weeks at temperatures about 20° C.

*Root description*.—Thick; typically whitish brown in color, actual color of the roots is dependent on substrate composition, water quality, fertilizer type and formulation, substrate temperature and physiological age of roots.

*Rooting habit*.—Freely branching; dense.

Plant description:

*Plant and growth habit*.—Upright and uniformly mounded plant habit; strong and sturdy stems; rapid growth rate and vigorous growth habit.

*Plant height*.—About 18 cm to 20 cm.

*Plant diameter or area of spread*.—About 45 cm to 50 cm.

Lateral branch description:

*Branching habit*.—Freely branching habit; when pinched, about eight lateral branches develop per plant.

*Length*.—About 16 cm to 18 cm.

*Diameter*.—About 5 mm to 7 mm.

*Internode length*.—About 3 cm to 5 cm.

*Texture*.—Smooth, glabrous; fully developed, woody.

*Aspect*.—Upright to about 20° from vertical.

*Strength*.—Strong, sturdy.

*Color*.—When developing: Close to 144B; at internodes, close to 187A to 187C; lenticels, close to 187A to 187C. Developed: Close to 144B; at the internodes, close to 187A to 187C; when woody, close to 177C; lenticels, close to 187A to 187C.

Leaf description:

*Arrangement*.—Opposite, simple.

*Length*.—About 7 cm to 10 cm.

*Width*.—About 5 cm to 6 cm.

*Shape*.—Ovate.

*Apex*.—Acute to cuspidate.

*Base*.—Obtuse.

*Margin*.—Dentate.

*Texture, upper surface*.—Smooth, glabrous.

*Texture, lower surface*.—Rugose, glabrous.

*Venation pattern*.—Pinnate.

*Color*.—Developing and fully expanded leaves, upper surface: Close to 147A; venation, close to 145B. Developing and fully expanded leaves, lower surface: Close to 147D; venation, close to 145C.

*Petioles*.—Length: About 1.5 cm to 2 cm. Diameter: About 3 mm. Texture, upper and lower surfaces: Smooth, glabrous. Color, upper and lower surfaces: Close to 145B.

Flower description:

*Flower type and habit*.—Double showy sterile flowers arranged on lacecap-type terminal panicles; to date, fertile flower development has not been observed on plants of the new *Hydrangea*; panicles flattened globular in shape; flowers face upright to outwardly depending on their position in the inflorescence.

*Fragrance*.—None detected.

*Natural flowering season*.—Plants begin flowering about three months after planting; flowering begins in the early summer and is continuous throughout the summer in Northern Europe.

*Flower longevity*.—Sterile flowers last about four months on the plant, sterile flowers persistent.

*Quantity of flowers*.—Freely flowering habit; about 170 to 210 sterile flowers develop per panicle.

*Panicle height*.—About 6 cm to 8 cm.

*Panicle diameter*.—About 18 cm to 20 cm.

*Sterile flower buds*.—Length: About 5 mm. Diameter: About 5 mm. Shape: Spherical. Color: Close to 145C.

*Sterile flower diameter*.—About 2 cm to 3 cm.

*Sterile flower depth* (*height*).—About 1 cm to 1.5 cm.

*Petals, sterile flowers*.—To date, petal development has not been observed on plants of the new *Hydrangea*.

*Sepals, sterile flowers*.—Quantity and arrangement: About 14 in about three whorls. Length, outer whorl: About 1.5 cm to 2.5 cm. Length, inner whorls: About 1 cm to 2 cm. Width, outer whorl: About 1 cm to 1.5 cm. Width, inner whorls: About 0.5 cm to 1 cm. Shape: Ovate. Apex: Acute. Base: Cuneate. Margin: Entire. Texture, upper and lower surfaces: Smooth, glabrous. Color: When opening, upper and lower surfaces: Close to 144C and 72D. Fully opened, upper surface: Close to 67C; color does not change with development; when "blued", distally becoming closer to 86B and 72B. Fully opened, lower surface: Close to N57D; color does not change with development.

*Pedicels, sterile flowers*.—Length: About 2 cm to 3.5 cm. Diameter: About 2 mm. Strength: Strong. Aspect: Erect to about 45° from vertical. Texture: Smooth, glabrous. Color: Close to 67D.

*Reproductive organs, sterile flowers*.—Stamens: To date, stamen development has not been observed on plants of the new *Hydrangea*. Pistils: Pistil quantity per flower: Three. Pistil length: About 1 mm. Stigma shape: Oval. Stigma color: Close to 150D. Style length: About 1 mm. Style color: Close to 145D. Ovary color: Close to 145D.

*Seeds*.—To date, seed development has not been observed on plants of the new *Hydrangea*.

Pathogen & pest resistance: Under commercial production conditions, plants of the new *Hydrangea* have not been observed to be resistant to pathogens and pests common to *Hydrangea* plants to date.

Temperature tolerance: Plants of the new *Hydrangea* have been shown to be tolerant to temperatures ranging from about 3° C. to about 38° C.

It is claimed:

1. A new and distinct *Hydrangea* plant named 'H218917' as illustrated and described.

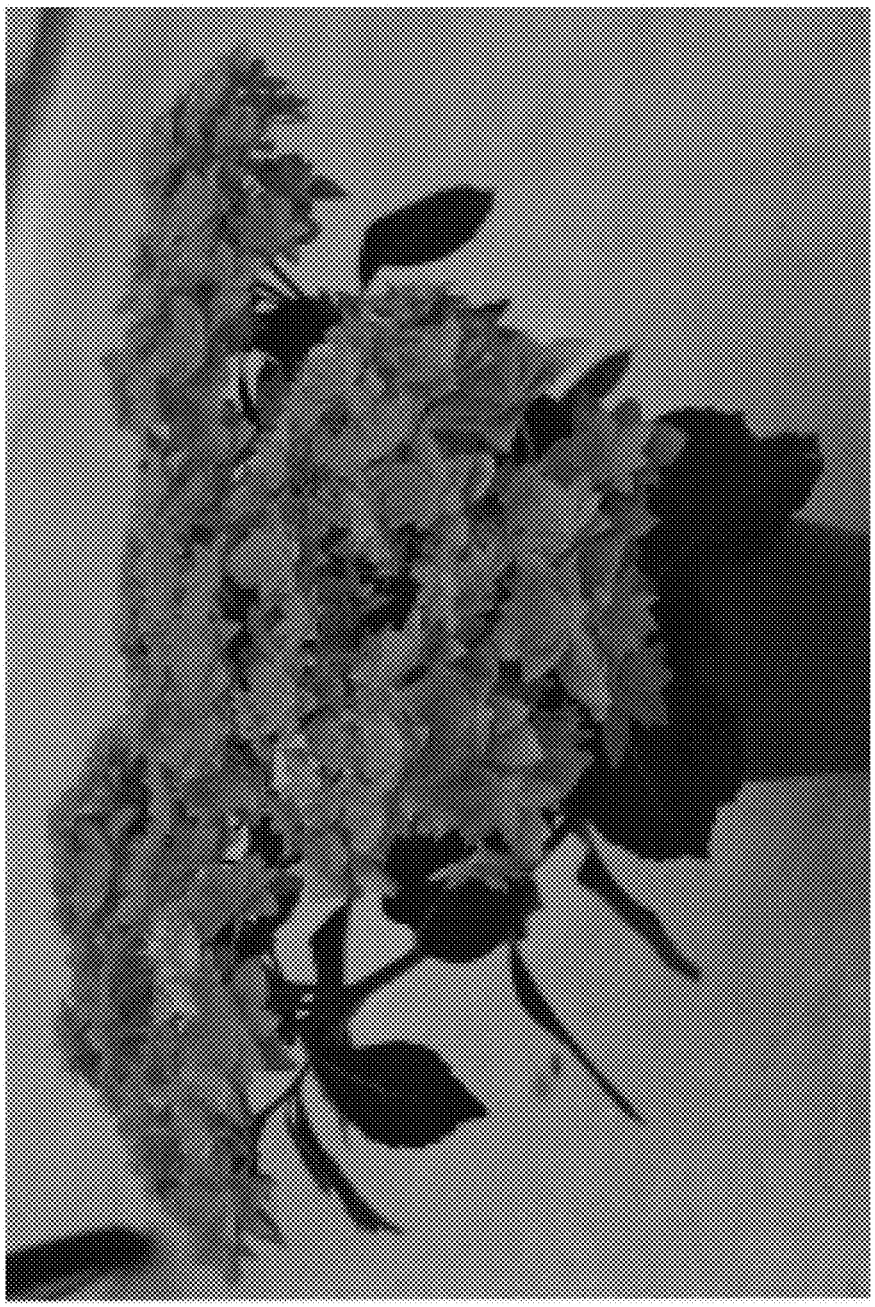

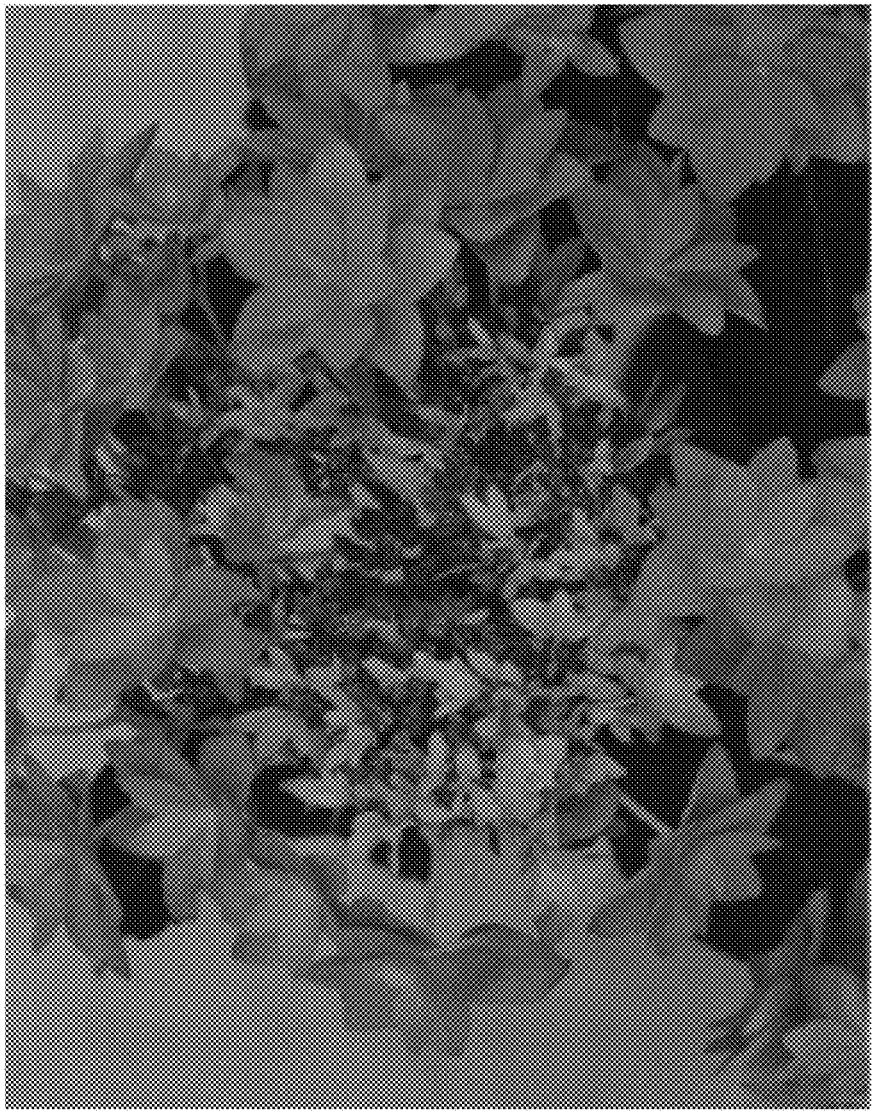

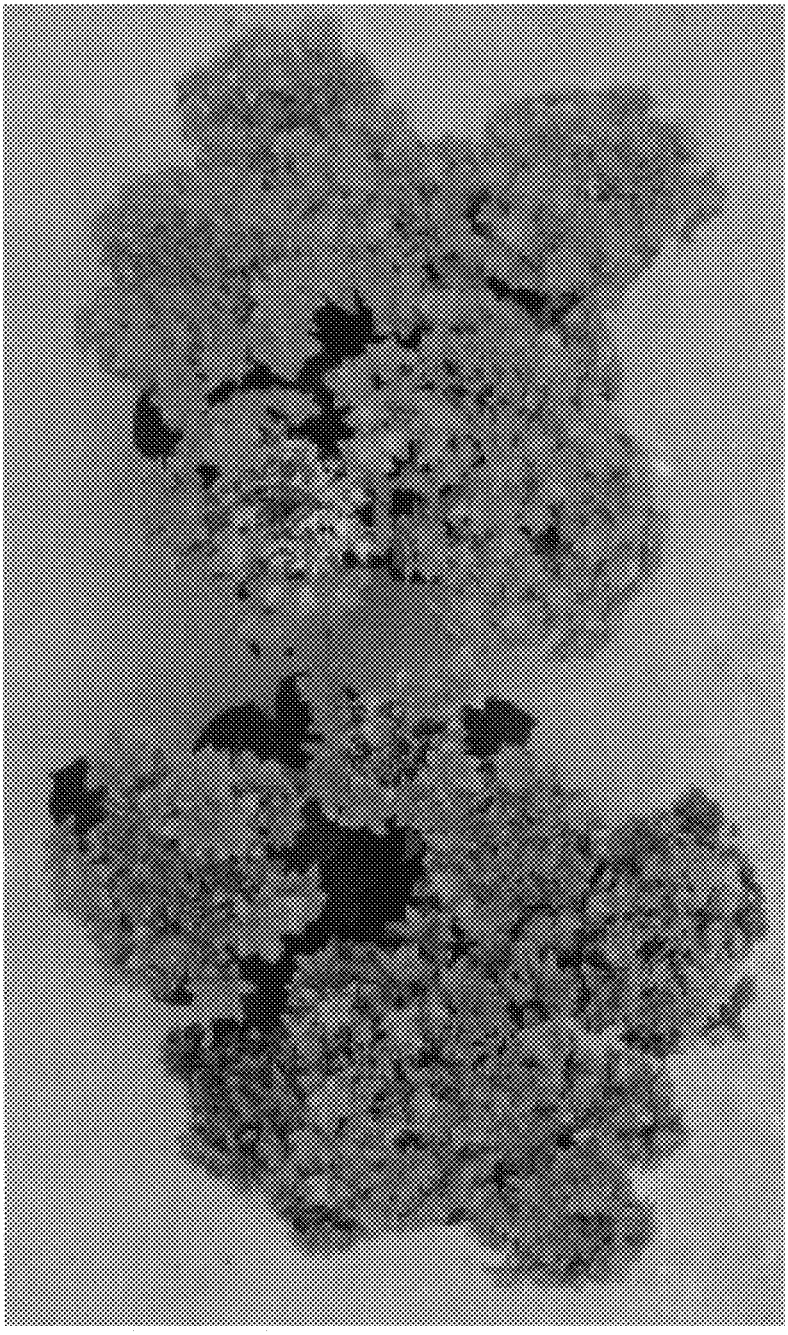

* * * * *